US012564561B2

(12) United States Patent
Caronzolo et al.

(10) Patent No.: US 12,564,561 B2
(45) Date of Patent: Mar. 3, 2026

(54) DILUTE READY TO USE LARGE VOLUME CONTAINERS OF PHENYLEPHRINE

(71) Applicant: Sintetica S.A., Mendrisio (CH)

(72) Inventors: Nicola Caronzolo, Bissone (CH);
Elisabetta Donati, Mendrisio (CH);
Clara Bianchi, Torno (IT)

(73) Assignee: Sintetica S.A., Mendrisio (CH)

( * ) Notice: Subject to any disclaimer, the term of this patent is extended or adjusted under 35 U.S.C. 154(b) by 906 days.

(21) Appl. No.: 17/670,620

(22) Filed: Feb. 14, 2022

(65) Prior Publication Data

US 2022/0257537 A1 Aug. 18, 2022

Related U.S. Application Data

(60) Provisional application No. 63/149,373, filed on Feb. 15, 2021.

(51) Int. Cl.
| | |
|---|---|
| *A61K 31/137* | (2006.01) |
| *A61K 47/54* | (2017.01) |
| *A61M 5/14* | (2006.01) |

(52) U.S. Cl.
CPC .......... *A61K 31/137* (2013.01); *A61K 47/547* (2017.08); *A61M 5/14* (2013.01)

(58) Field of Classification Search
CPC ...... A61K 31/137; A61K 47/547; A61K 9/08; A61K 9/0019; A61M 5/14
See application file for complete search history.

(56) References Cited

U.S. PATENT DOCUMENTS

| | | | |
|---|---|---|---|
| 2003/0216413 A1 | 11/2003 | Root-Bernstein et al. | |
| 2018/0333374 A1 | 11/2018 | Taneja | |
| 2020/0338020 A1* | 10/2020 | Dusci ..................... | A61K 47/02 |
| 2021/0228507 A1† | 7/2021 | Puri | |

FOREIGN PATENT DOCUMENTS

| | | | |
|---|---|---|---|
| WO | 2011/156481 A2 | 12/2011 | |
| WO | 2017/007957 A1 | 1/2017 | |
| WO | WO-2021150747 A1 * | 7/2021 | ............. A61K 47/20 |

OTHER PUBLICATIONS

AJHSP; Stability of phenylephrine hydrochloride injection in poly-propylene syringes; https://doi.org/10.2146/ajhp060139 (Year: 2007).*
https://www.lyondellbasell.com/en/products-technology/polymers/resin-type/polypropylene-random-copolymer/#:~:text=CustomerXPRESS%20Login,resistance%20amongst%20Polypropylene%20resin%20types (Year: 2025).*
The Future of Intravenous Therapy: Non-PVC IV Bags—A Blog by IHR Insights https://medium.com/@ihrinsights/the-future-of-intravenous-therapy-non-pvc-iv-bags-96a077d3599f (Year: 2023).*
https://www.vonco.com/product/iv-bags/?gad_source=1&gad_campaignid=21891691394&gbraid=0AAAAAp- AcdEa- LgDR7tcDBTMLKSH2XbW5tz&gclid=Cj0KCQjw0qTCBhCmAR IsAAj8C4a748af5fAh3hRZgghfDegfgZWgWx1SJYfllAIVDspC2b rMy3IPUP4aAtMYEALw_wcB (Year: 2025 ).*
Ahmad, Iqbal et al.; Photostability and Photostabilization of Drugs and Drug Products; Hindawi Publishing Corporation International Journal of Photoenergy, vol. 2016, Article ID 8135608, http://dx. doi.org/10.1155/2016/8135608, 20pp.
Athenex, 503B; PHENYLephrine, The Next Generation of Pharmacy Innovation; 2018 APS-PRM-008; 2 pp.
Larmene-Beld; Karin H.M. et al.; Prefilled Cyclic Olefin Sterilized Syringes of Norepinephrine Injection Solution Do Not Need to be Stabilized by Antioxidants; AAPS PharmSciTech (2020) 21: 247; DOI: 10.1208/s12249-020-01784-z; Research Article; 6 pp.
Biorphen (phenylephrine hydrochloride) injection; Label; Highlights of Prescribing Information; Oct. 2019; Manufactured for: Eton Pharmaceuticals, Inc.9 pp.
Cantrell Drug Company; Phenylephrine HCL 10 mg—phenylephrine hcl injection, solution; Label; Apr. 2013; 2 pp.
Cantrell Drug Company; Phenylephrine HCL 40 mg—phenylephrine hcl injection, solution; Label; Aug. 2015; 2 pp.
Cantrell Drug Company; Phenylephrine HCL 30 mg—phenylephrine hcl injection, solution; Label; Jan. 2015; 2 pp.
CAPS Pharmacy Catalogue; Oct. 2020; 10pp.
De Luca, Michele et al.; Photostabilization Studies of Antihypertensive 1,4-Dihydropyridines Using Polymeric Containers; Elsevier; International Journal of Pharmaceutics 505 (2016) 376-382.
Dib, Shelby Anne; Thesis; Stability of Phenylephrine Hydrochloride in Polyvinyl Chloride Bags; 2019, Ohio State University, Graduate Program in Dentistry; 37 pp.
Jansen, Josiah J. et al.; Evaluation of Phenylephrine Stability in Polyvinyl Chloride Bags; Hosp Pharm 2014;49(5):455-457; 2014 © Thomas Land Publishers, Inc.; www.hospital-pharmacy.com; doi: 10.1310/hpj4905-455; 3 pp.
Buntinx, Mieke; et al.; Evaluation of the Thickness and Oxygen Transmission Rate before and after Thermoforming Mono- and Multi-layer Sheets into Trays with Variable Depth; Polymers 2014, 6, 3019-3043; doi:10.3390/polym6123019; 25pp.
Patil; P. N.; Steric Aspects of Adrenergic Drugs. VIII. Optical Isomers of Beta Andrenergic Receptor Antagonists; The Journal of Pharmacology and Experimental Therapeutics, vol. 160; No. 2; 1968; 7 pp.
Patil, P.N. et al.; Steric Aspects of Adrenergic Drugs. IX. Pharmacologic and Histochemical Studies on Isomers of Cobefrin (a-Methylnorepinephrine); The Journal of Pharmacology and Experimental Therapeutics, vol. 161, No. 2; 1968; 17 pp.
Hall, M. et al.; A use of the isomeric ratio as a criterion to differentiate adrenergic receptors; Letters to the Editor, J. Pharm. Pharmac., 1969,21, 628; 2pp.
Renfrew, C.W. et al.; A qualitative investigation into the physical stability of polypropylene and polyethylene in liquid softurane and sevoflurane; Anaesthesia, 2000, 55, pp. 793-797.

(Continued)

*Primary Examiner* — Robert A Wax
*Assistant Examiner* — Andre Mach
(74) *Attorney, Agent, or Firm* — Clark G. Sullivan

(57) ABSTRACT

Ready to use semi-naked dilute solutions of phenylephrine, resistant to oxidative degradation when packaged in transparent or translucent collapsible polypropylene bags and terminally sterilized, without the need for an aluminum over-wrap, oxygen scavengers, oxygen impermeable polypropylene, antioxidants, or chelating agents.

4 Claims, 3 Drawing Sheets
(1 of 3 Drawing Sheet(s) Filed in Color)

(56)                    References Cited

OTHER PUBLICATIONS

Trommer, Hagen et al.; Investigating the degradation of the sympathomimetic drug phenylephrine by electrospray ionisation-mass spectrometry; Elsevier; Journal of Pharmaceutical and Biomedical Analysis 52 (2010) 203-209.

Vazculep (phenylephrine hydrochloride) Injection for intravenous use; Initial U.S. Approval: 1954; Label; Jun. 2014; 10 pp.

International Application No. PCT/IB2022/051318 filed Feb. 15, 2022; International Search Report and Written Opinion; ISA/EP; May 23, 2022; 7 pp.

Declaration of Nathaniel E Frank-White and Exhibit A Thereof, Technoflex Website Art, 9 pages, Nov. 30, 2022.†

* cited by examiner
† cited by third party

Batch 10188 - Trends at 60 °C stability Conditions

Batch 10188 - Trends at 40 °C stability Conditions

Batch 10188 - Trends at 40 °C stability Conditions

Batch 10188 - Trends at 25 °C stability Conditions

DILUTE READY TO USE LARGE VOLUME CONTAINERS OF PHENYLEPHRINE

FIELD OF THE INVENTION

The present invention relates to dilute ready to use large volume containers of phenylephrine, particularly phenylephrine hydrochloride in shelf-stable ready to use intravenous drip bags, suitable for continuous intravenous infusion without further dilution prior to administration.

BACKGROUND

Phenylephrine is a synthetic sympathomimetic agent with various medical uses, including, in hospital settings, maintenance of adequate blood pressure during anesthesia and treatment of vascular failure in shock and shock-like states. Parenteral formulations are commercially available in small glass vials (1, 5, and 10 ml) and intravenous ready to use ("RTU") PVC drip bags (>100 ml), but only the small glass vials remain chemically stable for prolonged periods of time. While the small glass vials are stable, they suffer from the fact that they must be reconstituted and diluted into larger containers for continuous infusion or, if they are sufficiently dilute for direct infusion, multiple vials must typically be administered.

This instability is commonly attributed to oxidation of phenylephrine and to photolytic degradation. Various techniques to overcome this instability have been investigated. Dibbs 2019 examined the stability of phenylephrine HCl in 100 ml 0.9% sodium chloride RTU PVC bags, at a concentration of 0.1 mg/ml, under four different storage conditions, a 52° C. water bath, room temperature (23° C.-25° C.) exposed to direct fluorescent light, room temperature (23° C.-25° C.) with no light, and refrigerated at 4° C., over a total period of 138 days, and concluded that the formulation was only stable when refrigerated or protected from light at room temperature. The formulation was not stable when exposed to fluorescent lighting at room temperature.

Consistent with this finding, Cantrell Drug Co., markets several different concentrations of large RTU bags of phenylephrine HCl in opaque bags that prevent entry of light. These opaque bags are undesirable because they prevent the detection of impurities or discoloration in the bag's contents. Even with opaque covering, these large volume bags uniformly have a much shorter shelf life, and they commonly include multiple undesirable excipients to ensure the stability and other attributes of the formulation. Cantrell's drug products, for example, contain sodium chloride, sodium citrate, sodium metabisulfite, citric acid, and sodium hydroxide.

What is needed are dilute RTU bags of phenylephrine that need not be replaced when used in the operating room, that remain stable over time even when confronted with oxygen permeation, and that are sufficiently translucent or transparent to detect the presence of impurities in the bag or discoloration of the bag's contents.

SUMMARY OF INVENTION

The inventors have performed extensive evaluations of translucent polypropylene films, having different levels of oxygen permeability, but similar levels of translucency, and have unexpectedly discovered that dilute phenylephrine solutions can be stored for prolonged periods in polypropylene bags, even when the polypropylene admits lights, and even when the formulation lacks common stabilizing excipients such as sulfites and chelating agents. Without wishing to be bound by any particular theory, it is believed that translucent polypropylene inhibits the passage of light having a wavelength that destabilizes the phenylephrine. The stabilizing influence can be seen even when using semi-naked formulations of phenylephrine HCl that omit, among other ingredients, stabilizing and alkalizing agents such as sulfites and sodium hydroxide, and even when polypropylene is used having only moderate blockage of oxygen transmission.

Thus, in a first principal embodiment, the invention provides a drug product in a hermetically sealed intravenous ready to use collapsible drip bag, wherein: (a) the bag comprises two opposed walls sealed around their peripheries comprising an inner ply of translucent or transparent polypropylene; (b) the bag defines an interior volume; (c) the interior volume comprises: (i) a liquid volume comprising from 75 to 550 ml or from 100 to 350 ml or from 250 to 325 ml of a liquid formulation; (ii) a gaseous headspace occupying from 0 to 25% or from 2 to 15% of the interior volume; (d) the liquid formulation comprises: (i) phenylephrine or a pharmaceutically acceptable salt thereof at a concentration of from 0.001 to 2.0 mg/ml or from 0.01 to 0.8 mg/ml; (ii) a tonicity agent; (iii) an acidic pH adjusting agent; and (iv) water; (e) the liquid formulation has a pH of from 2.5 to 6.5, from 2.6 to 5.5, from 2.7 to 5.0, from 2.8 to 4.5, from 3.0 to 6.5, from 3.0 to 5.5, from 3.0 to 5.0, from 3.0 to 4.5, from 3.0 to 3.8, from 3.0 to 3.6, from 3.0 to 3.4, or from 3.0 to 3.2; and (f) the liquid formulation excludes sulfites and/or sodium hydroxide. In one preferred embodiment, the bag or the bag wall has an oxygen transmission rate greater than 0.5, 1.0, 20, 100, 500, 1000, or even 4000 $cm^3 \cdot 20$ $\mu m/m^2 \cdot day \cdot atm$, preferably less than 40,000 or 10,000 $cm^3 \cdot 20$ $\mu m/m^2 \cdot day \cdot atm$, at room temperature and atmospheric pressure.

A second principal embodiment related to the semi-naked formulations used in the RTU bags of the current invention. Thus, in a second principal embodiment, the invention provides a drug product in a hermetically sealed intravenous ready to use collapsible drip bag, wherein: (a) the bag defines an interior volume; (b) the interior volume comprises: (i) a liquid volume comprising from 75 to 550 ml or from 100 to 350 ml or from 250 to 325 ml of a liquid formulation; (ii) a gaseous headspace occupying from 0 to 25% or from 2 to 15% of the interior volume; (c) the liquid formulation comprises: (i) phenylephrine or a pharmaceutically acceptable salt thereof at a concentration of from 0.001 to 2.0 mg/ml or from 0.01 to 0.8 mg/ml; (ii) a tonicity agent; (iii) an acidic pH adjusting agent; and (iv) water; (d) the liquid formulation has a pH of from 2.5 to 6.5, from 2.6 to 5.5, from 2.7 to 5.0, from 2.8 to 4.5, from 3.0 to 6.5, from 3.0 to 5.5, from 3.0 to 5.0, from 3.0 to 4.5, from 3.0 to 3.8, from 3.0 to 3.6, from 3.0 to 3.4, or from 3.0 to 3.2; and (e) the liquid formulation excludes sulfites and/or sodium hydroxide. In one preferred embodiment, the bag or the bag wall has an oxygen transmission rate greater than 0.5, 1.0, 20, 100, 500, 1000, or even 4000 $cm^3 \cdot 20$ $\mu m/m^2 \cdot day \cdot atm$, preferably less than 40,000 or 10,000 $cm^3 \cdot 20$ $\mu m/m^2 \cdot day \cdot atm$, at room temperature and atmospheric pressure.

A third embodiment relates to methods of making the drug products of the present invention, and to drug products made thereby. Thus in a third principal embodiment the invention provides a method of making a phenylephrine drug product in an intravenous ready to use collapsible drip bag comprising: (a) dissolving phenylephrine or a pharmaceutically acceptable salt thereof, a tonicity agent, and an acidic pH adjusting agent in water to produce a phenyleph-rine liquid formulation at a concentration of from 0.001 to 2.0 mg/ml or from 0.01 to 0.8 mg/ml; (b) distributing from 75 to 550 ml or from 100 to 350 ml or from 250 to 325 ml of the phenylephrine liquid formulation and an inert gas into the bag, such that the percentage of the bag's volume occupied by the headspace is from 0 to 25% or from 2 to 15%; and (c) hermetically sealing the bag; wherein: (i) the liquid formulation excludes sulfites and/or sodium hydrox-ide; and/or (ii) the liquid formulation has a pH of from 3.0 to 6.5. In a particularly preferred method, the bag comprises two opposed walls sealed around their peripheries compris-ing an inner ply of translucent or transparent polypropylene. In another preferred embodiment, the bag or the bag wall has an oxygen transmission rate greater than 0.5, 1.0, 20, 100, 500, 1000, or even 4000 cm$^3$·20 μm/m$^2$·day·atm, preferably less than 40,000 or 10,000 cm$^3$·20 μm/m$^2$·day·atm, at room temperature and atmospheric pressure.

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate several embodiments of the invention and together with the descrip-tion serve to explain the principles of the invention.

4

DETAILED DESCRIPTION

Definitions and Use of Terms

Figure 1:
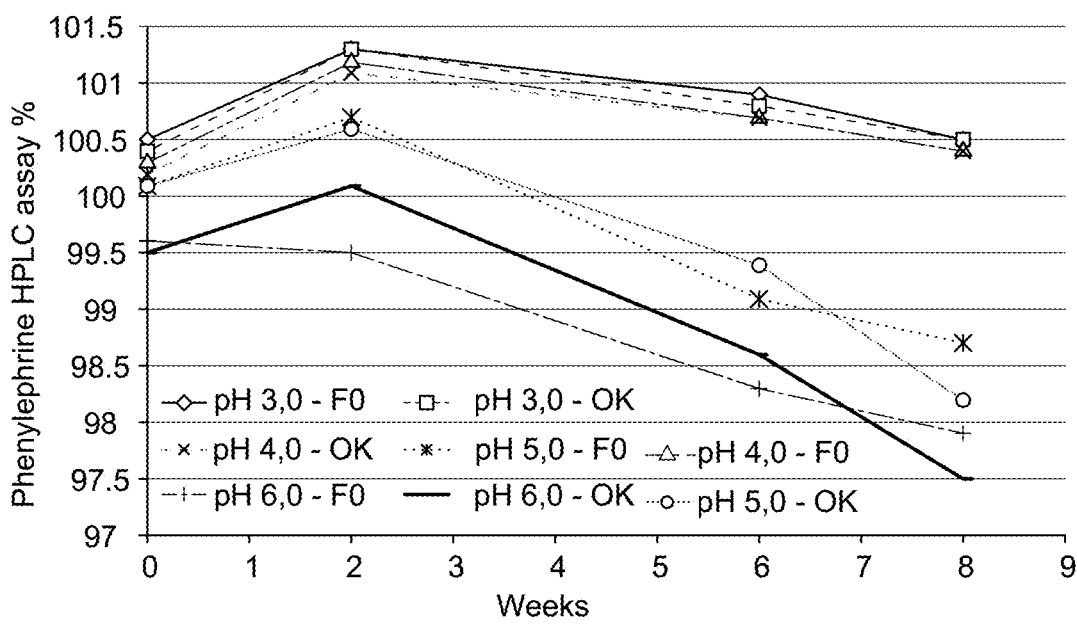
FIG. 1 is a graphical depiction of phenylephrine concen-trations measured by HPLC over time for the semi-naked formulations of the present invention, at pH values ranging from 3.0 to 6.0, manufactured using overkill terminal ster-ilization and FO sterilization, as tested and described in Example 3.

Throughout this application, various publications are ref-erenced. The disclosures of these publications in their entire-ties are hereby incorporated by reference into this applica-tion in order to more fully describe the state of the art to which this invention pertains. The references disclosed are also individually and specifically incorporated by reference herein for the material contained in them that is discussed in the sentence in which the reference is relied upon.

As used in the specification and claims, the singular forms a, an, and the include plural references unless the context clearly dictates otherwise. For example, the term "a speci-fication" refers to one or more specifications for use in the presently disclosed methods and systems. "A hydrocarbon" includes mixtures of two or more such hydrocarbons, and the like. The word "or" or like terms as used herein means any one member of a particular list and also includes any combination of members of that list.

As used in this specification and in the claims which follow, the word "comprise" and variations of the word, such as "comprising" and "comprises," means "including but not limited to," and is not intended to exclude, for example, other additives, components, integers or steps. When an element is described as comprising one or a plurality of components, steps or conditions, it will be understood that the element can also be described as "consisting of" or "consisting essentially of" the component, step or condition, or the plurality of components, steps or conditions.

When ranges are expressed herein by specifying alterna-tive upper and lower limits of the range, it will be understood that the endpoints can be combined in any manner that is mathematically feasible. Thus, for example, a range of from 50 or 80 to 100 or 70 can alternatively be expressed as a series of ranges of from 50 to 100, from 50 to 70, and from 80 to 100. When a series of upper bounds and lower bounds are related using the phase "and" or "or", it will be under-stood that the upper bounds can be unlimited by the lower bounds or combined with the lower bounds, and vice versa. Thus, for example, a range of greater than 40% and/or less than 80% includes ranges of greater than 40%, less than 80%, and greater than 40% but less than 80%.

When an element of a process or thing is defined by reference to one or more examples, components, properties or characteristics, it will be understood that any one or combination of those components, properties or character-istics can also be used to define the subject matter at issue. This might occur, for example, when specific examples of an element are recited in a claim (as in a Markush grouping), or an element is defined by a plurality of characteristics. Thus, for example, if a claimed system comprises element A defined by elements A1, A2 and A3, in combination with element B defined by elements B1, B2 and B3, the invention will also be understood to cover a system defined by element A without element B, a system in which element A is defined by elements A1 and A2 in combination with element B defined by elements B2 and B3, and all other possible permutations.

When used herein the term "about" will compensate for variability allowed for in the pharmaceutical industry and inherent in products in this industry, such as differences in product strength due to manufacturing variation and time-induced product degradation. The term allows for any varia-tion which in the practice of good manufacturing practices would allow the product being evaluated to be considered therapeutically equivalent or bioequivalent in humans to the recited strength of a claimed product. Alternatively, the term "about" can be substituted by +/−10% or +/−5%.

The phrase "acceptable" as used in connection with compositions of the invention, refers to molecular entities and other ingredients of such compositions that are physiologically tolerable and do not typically produce untoward reactions when administered to a subject (e.g., a mammal such as a human).

When published test methodologies and diagnostic instruments are referred to herein, it will be understood that the test methodology or diagnostic instrument is performed based on the version in effect on Jan. 1, 2021, unless otherwise stated to the contrary herein.

Oxygen transmission rates described herein can be measured using the methods described by ASTM International (West Conshohocken Pa., USA), according to the standard in effect for the particular material being analyzed.

Translucent means admitting or diffusing light so that objects beyond cannot be clearly distinguished. Transparent means having the property of transmitting light without appreciable scattering so that bodies lying beyond are entirely visible. For purposes of this invention, the bags depicted in FIG. 5 would be considered translucent because the letters beyond the bag can be distinguished, even though the identity of the letters is difficult to discern.

Within the present invention, "injectable" means suitable to be injected into a patient (human or animal). Typically, the phenylephrine solution of the invention is administered by intravenous or intra-arterial injection. In certain embodiments, there is provided an infusion of a therapeutically active amount of the phenylephrine solution according to the invention.

Within the present invention, the term "alkalizing agent" or "basic pH adjusting agent" refers to any inactive excipient used in the pharmaceutical arts to increase the pH of a liquid injectable formulation. A comprehensive listing of such agents, including acceptable concentrations, can be found in the United States Food and Drug Administration's ("FDA's") Inactive Ingredients Database as of Jan. 1, 2021. Examples include ammonia, calcium hydroxide, diethanolamine, monoethanolamine, potassium bicarbonate, potassium citrate, potassium hydroxide, sodium bicarbonate, sodium borate, sodium carbonate, sodium citrate dihydrate, sodium hydroxide, and triethanolamine, in the concentrations cited in FDA's Inactive Ingredients Database for injectable formulations.

Within the present invention, the term "antioxidant" shall mean any antioxidant known in the art which is added to a solution of phenylephrine of a pharmaceutically acceptable salt thereof in order to protect phenylephrine from oxidation. Examples of antioxidants are sulfite(s) or ascorbic acid, or the antioxidants disclosed in US2016/0058715A1, see in particular paragraph [0016] thereof, or other antioxidants known in the art. A more comprehensive listing of antioxidants appears in Rowe et al., Handbook of Pharmaceutical Excipients, 6th Edition 2009, which includes alpha tocopherol, ascorbic acid, ascorbyl palmitate, butylated hydroxyanisole, butylated hydroxytoluene, carbon dioxide, chelating agents, citric acid monohydrate, erythorbic acid, ethyl oleate, fumaric acid, malic acid, methionine, monothioglycerol, phosphoric acid, potassium metabisulfite, propionic acid, propyl gallate, sodium ascorbate, sodium bisulfite, sodium formaldehyde sulfoxylate, sodium metabisulfite, sodium sulfite, sodium thiosulfate, sulfur dioxide, tartaric acid, thymol, tocopherol, vitamin E, vitamin E, and polyethylene glycol succinate, preferably in the concentrations cited in FDA's Inactive Ingredients Database for injectable formulations.

When a formulation is said to lack antioxidants in this document, it will be understood that the formulation could be defined as lacking one or any combination of antioxidants, or any antioxidants whatsoever, as that term is traditionally used in the art. In addition, it will be understood that terminology communicating a lack of antioxidants encompasses a subembodiment and can be replaced with terminology communicating the lack of sulfites, particularly sodium metabisulfite.

Within the present invention, the term "chelating agent (s)" shall mean any chelating agent known in the art which can be added to a solution of phenylephrine of a pharmaceutically acceptable salt thereof in order to protect phenylephrine from degradation. Examples include in particular metal ion chelators, such as EDTA, EGTA, DTPA and the like; see e.g. WO2018/140894A1, in particular paragraph [0024] thereof. A more comprehensive listing of chelating agents appears in Rowe et al., Handbook of Pharmaceutical Excipients, 6th Edition 2009, which includes antioxidants, citric acid, disodium edetate, edetate calcium disodium, edetic acid, fumaric acid, malic acid, maltol, pentetic acid, sodium edetate, trisodium edetate preferably in the concentrations cited in FDA's Inactive Ingredients Database for injectable formulations.

When a formulation is said to lack chelating agents in this document, it will be understood that the formulation could be defined as lacking one or any combination of chelating agents, or any chelating agent whatsoever, as that term is traditionally used in the art, as described, for example, in Rowe et al., Handbook of Pharmaceutical Excipients, 6th Edition 2009. In addition, it will be understood that terminology communicating a lack of chelating agents encompasses a subembodiment and can be replaced with terminology communicating the lack of edetic acid or any salt thereof such as disodium edetate (collectively "EDTA").

The concentrations of phenylephrine or a pharmaceutically acceptable salt thereof are indicated herein as mg or μg calculated based on the weight of the species in which the phenylephrine is present, per ml of the total solution, unless indicated otherwise. Thus, for example, if the phenylephrine is present as the hydrochloride salt, the weight or concentration will be based on the weight of the entire phenylephrine hydrochloride molecule.

As is conventional in the pharmaceutical arts, when a salt is said to be in solution in this document, it will be understood that the salt may have disassociated into its respective counterions. In like manner, when the weight or concentration of a salt is expressed for a solution, the weight or concentration will be understood to include the respective weight of each counterion, even though the counterions may have disassociated in solution.

Discussion

In a first principal embodiment the invention provides a drug product in a hermetically sealed intravenous ready to use collapsible drip bag, wherein: (a) the bag comprises two opposed walls sealed around their peripheries comprising an inner ply of translucent or transparent polypropylene; (b) the bag defines an interior volume; (c) the interior volume comprises: (i) a liquid volume comprising from 75 to 550 ml or from 100 to 350 ml or from 250 to 325 ml of a liquid formulation; (ii) a gaseous headspace occupying from 0 to 25% or from 2 to 15% of the interior volume; (d) the liquid formulation comprises: (i) phenylephrine or a pharmaceutically acceptable salt thereof at a concentration of from 0.001 to 2.0 mg/ml or from 0.01 to 0.8 mg/ml; (ii) a tonicity agent; (iii) an acidic pH adjusting agent; and (iv) water; (e) the liquid formulation has a pH of from 2.5 to 6.5, from 2.6 to 5.5, from 2.7 to 5.0, from 2.8 to 4.5, from 3.0 to 6.5, from 3.0 to 5.5, from 3.0 to 5.0, from 3.0 to 4.5, from 3.0 to 3.8, from 3.0 to 3.6, from 3.0 to 3.4, or from 3.0 to 3.2; and (f) the liquid formulation excludes sulfites and/or sodium hydroxide. In one preferred embodiment, the bag or bag wall has an oxygen transmission rate greater than 0.5, 1.0, 20, 100, 500, 1000, or even 4000 $cm^3 \cdot 20$ $\mu m/m^2 \cdot day \cdot atm$, preferably less than 40,000 or 10,000 $cm^3 \cdot 20$ $\mu m/m^2 \cdot day \cdot atm$, at room temperature and atmospheric pressure.

In a second principal embodiment directed to the formulation itself, the invention provides a drug product in a hermetically sealed intravenous ready to use collapsible drip bag, wherein: (a) the bag defines an interior volume; (b) the interior volume comprises: (i) a liquid volume comprising from 75 to 550 ml or from 100 to 350 ml or from 250 to 325 ml of a liquid formulation; (ii) a gaseous headspace occupying from 0 to 25% or from 2 to 15% of the interior volume; (c) the liquid formulation comprises: (i) phenylephrine or a pharmaceutically acceptable salt thereof at a concentration of from 0.001 to 2.0 mg/ml or from 0.01 to 0.8 mg/ml; (ii) a tonicity agent; (iii) an acidic pH adjusting agent; and (iv) water; (d) the liquid formulation has a pH of from 2.5 to 6.5, from 2.6 to 5.5, from 2.7 to 5.0, from 2.8 to 4.5, from 3.0 to 6.5, from 3.0 to 5.5, from 3.0 to 5.0, from 3.0 to 4.5, from 3.0 to 3.8, from 3.0 to 3.6, from 3.0 to 3.4, or from 3.0 to 3.2; and (e) the liquid formulation excludes sulfites and/or sodium hydroxide. In one preferred embodiment, the bag or bag wall has an oxygen transmission rate greater than 0.5, 1.0, 20, 100, 500, 1000, or even 4000 $cm^3 \cdot 20$ $\mu m/m^2 \cdot day \cdot atm$, preferably less than 40,000 or 10,000 $cm^3 \cdot 20$ $\mu m/m^2 \cdot day \cdot atm$, at room temperature and atmospheric pressure.

In a third principal embodiment the invention provides a method of making a phenylephrine drug product in an intravenous ready to use collapsible drip bag comprising: (a) dissolving phenylephrine or a pharmaceutically acceptable salt thereof, a tonicity agent, and an acidic pH adjusting agent in water to produce a phenylephrine liquid formulation at a concentration of from 0.001 to 2.0 mg/ml or from 0.01 to 0.8 mg/ml; (b) distributing from 75 to 550 ml or from 100 to 350 ml or from 250 to 325 ml of the phenylephrine liquid formulation and an inert gas into the bag, such that the percentage of the bag's volume occupied by the headspace is from 0 to 25% or from 2 to 15%; and (c) hermetically sealing the bag; wherein: (i) the liquid formulation excludes sulfites and/or sodium hydroxide; and/or (ii) the liquid formulation has a pH of from 3.0 to 6.5. In a particularly preferred method, the bag comprises two opposed walls sealed around their peripheries comprising an inner ply of translucent or transparent polypropylene. In another preferred embodiment, the bag or bag wall has an oxygen transmission rate greater than 0.5, 1.0, 20, 100, 500, 1000, or even 4000 $cm^3 \cdot 20$ $\mu m/m^2 \cdot day \cdot atm$, preferably less than 40,000 or 10,000 $cm^3 \cdot 20$ $\mu m/m^2 \cdot day \cdot atm$, at room temperature and atmospheric pressure.

Subembodiments

Various parameters can be used to further define the drug products and methods of manufacture of the current invention, as described in greater detail below. It will be understood that each of the subembodiments described below can be used to further define any of the principal embodiments, and that they can be combined in any combination to create new embodiments that are logically possible.

Any type container suitable for administration of large volumes of intravenous drug products are suitable for use in the present invention, although preferably the container is a ready to use collapsible drip bag. The interior volume of the containers of the current invention preferably ranges from 75 to 550 ml or from 100 to 350 ml or from 250 to 325 ml. A particularly preferred container has a nominal volume of 250 ml, and an absolute volume of from 260 to 300 ml. In some subembodiments the percentage of the container's volume occupied by the headspace is from 0 to 25%, with the remainder of the container's volume occupied by the drug solution. In other subembodiments the percentage of the container's volume occupied by the headspace is from 2 to 15%, with the remainder occupied by the drug solution. The headspace preferably consists essentially of an inert gas and trace amounts of oxygen. Preferred inert gases are selected from argon and nitrogen and combinations thereof, with nitrogen being particularly preferred.

The drug product can also be defined based on various formulation parameters. The phenylephrine, for example, can be present as any pharmaceutically acceptable salt. A particularly preferred salt is the hydrochloride salt.

The drug product can also be defined based on its stability, and the presence of impurities (i.e. by-products from the manufacturing process of phenylephrine, degradants of phenylephrine, and contaminants, but excluding residual solvents) in the solution. In preferred embodiments, the solution comprises no more than 1%, 0.5%, 0.2%, or even 0.1% (w/w) impurities and degradants of phenylephrine. In one preferred embodiment, the solution comprises no more than 1%, 0.5%, 0.2%, or even 0.1% (w/w) oxidative degradants of phenylephrine, especially phenylephrone.

The phenylephrine or phenylephrine salt can be present in various concentrations, always calculated based on the weight of the entire molecule, as mentioned in the definitions section of this document. In various embodiments, the concentration of phenylephrine is from 0.001 to 2.0 mg/ml or from 0.01 to 0.8 mg/ml. In particularly preferred embodiments, the concentration of phenylephrine is either 0.08 mg/ml or 0.4 mg/ml based on the weight of the hydrochloride salt.

The solution also preferably includes a pharmaceutically acceptable acid capable of adjusting the pH of the solution to a pH of from a pH of from 2.5 to 6.5, from 2.6 to 5.5, from 2.7 to 5.0, from 2.8 to 4.5, from 3.0 to 6.5, from 3.0 to 5.5, from 3.0 to 5.0, from 3.0 to 4.5, from 3.0 to 3.8, from 3.0 to 3.6, from 3.0 to 3.4, or from 3.0 to 3.2. Alternatively, the pH of the solution can range from 3.0 to 6.5. In some embodiments the liquid formulation has a pH of from 3.0 to 3.4 or from 3.0 to 3.2.

Suitable acids for adjusting the pH of the formulation include, for example, Acetic Acid, glacial, USP, Acetic Acid, NF, Citric Acid, anhydrous USP, Citric Acid, monohydrate USP, Fumaric Acid, NF, Hydrochloric Acid, diluted, NF, Hydrochloric Acid, NF, Lactic Acid, USP, Malic Acid, NF, Nitric Acid, NF, Phosphoric Acid, NF, Phosphoric Acid, diluted, NF, Propionic Acid, NF, Sodium phosphate monobasic, NF, Sulfuric Acid, NF, and Tartaric Acid, NF, with hydrochloric acid being most preferred.

The solution also preferably includes a pharmaceutically acceptable tonicity agent. Suitable tonicity agents can be found in the United States Pharmacopoeia and include, for example, dextrose, glycerin, mannitol, potassium chloride and sodium chloride, with sodium chloride being most preferred. The tonicity agent is preferably present in concentrations adequate to render the solution isotonic, i.e. about 290 mOsm/kg, or substantially isotonic, i.e. from 250 to 350 mOsm/kg.

In other embodiments, the formulation is defined based on what it omits. Thus, in some embodiments the liquid formulation excludes: (a) an antioxidant such as a sulfite; or (b) a chelating agent such as EDTA; or (c) an antimicrobial preservative; or (d) a basic pH adjusting agent such as sodium hydroxide; or (e) a combination thereof.

In one embodiment the liquid formulation excludes: (a) an antioxidant; (b) a chelating agent; and (c) an antimicrobial preservative. In another particular embodiment, the liquid formulations of the present invention exclude: (a) sulfites; (b) a chelating agent; (c) an antimicrobial preservative; and (d) a basic pH adjusting agent. In further embodiments the liquid formulations exclude sulfites and a basic pH adjusting agent. In still further embodiments the liquid formulations excludes sulfites and sodium hydroxide.

The formulations of the current invention can also be defined by the ingredients that they contain. Thus, the liquid formulations will generally contain an acidic pH adjusting agent such as hydrochloric acid. The liquid formulations will also generally contain a tonicity agent, preferably sodium chloride.

In some embodiments, the liquid formulations of the current invention further comprise nitrogen, exclude sulfites, and the acidic pH adjusting agent is hydrochloric acid. In other embodiments the liquid formulation further comprises nitrogen, the liquid formulation excludes sulfites and sodium hydroxide, and the acidic pH adjusting agent is hydrochloric acid.

The drug product can also be defined in terms of the container in which it is housed. Thus, for example, while a bag of the current invention can assume any configuration that permits filling, sealing, and subsequent access during use, in preferred embodiments the bag comprises two opposed walls sealed around their peripheries. The term "sealed around their peripheries" will allow for the placement of ports that permit the ingress and egress of fluid during filling and use. The term also allows for different bag designs that do not require heat or chemical sealing around the periphery, as long as the bag, when laid flat, defines two walls that cooperate to define a continuous inner volume without the possibility of fluid egress from the bag.

The walls of the bag are preferably translucent or transparent. In some embodiments the bag comprises two opposed walls sealed around their peripheries, wherein the walls comprise an interior ply of translucent or transparent polypropylene.

The walls of the bag are preferably constructed of a single ply of polypropylene or they may be constructed of multiplies incorporating a polypropylene inner ply with outer plies made of alternative plastics. Thus, in one embodiment the bag wall is a multi-ply product comprising two polypropylene layers and an ethylene vinyl alcohol layer sandwiched between the two polypropylene layers.

A preferred polypropylene is a translucent single ply random copolymer polypropylene such as the polypropylene ply based on a phthalate-free catalyst marketed by Total Research and Technology Feluy (Feluy, Belgium) under the trade name Polypropylene Aceso® PPM R020 S01. A particularly preferred material is the single ply random copolymer polypropylene, having substantially the properties described in Table 2a.

When a multi-lay bag is employed, a preferred material for the second ply is an ethylene vinyl alcohol copolymer having the structure:

$$-[CH_2-CH_2]_n-[CH(OH)-CH_2]_m- \text{ or } -[CH_2-CH_2]_n-[CH_2-CH(OH)]_m-$$

comprising less than 35 or 30 or mol % ethylene, preferably about 27 mol % ethylene. A particularly preferred material is an ethylene vinyl alcohol copolymer comprising 27 mol % ethylene, having substantially the physical properties reported in Table 4b.

In other embodiments the material used for the bag wall is defined based on its optical properties. In one particular embodiment the bag exhibits the optical properties of one or both of the bags depicted in FIG. 5. In another particular embodiment, the bag exhibits the optical properties of the material described in Table 4a and/or 4b. Optionally, the optical properties can be determined by the methods described in ASTM D 1003-61, and the plastic will have substantially the same haze and luminous transmittance values as one or both of the translucent polypropylene depicted in FIG. 5 or described in Table 4a and/or Table 4b. For purposes of this invention, it will be understood that the bags depicted in FIG. 5 have substantially equivalent optical properties.

Still further subembodiments relate specifically to the method of manufacturing the bags of the current invention. Thus, in any of the methods of the current invention, the manufacturing process is undertaken in the presence of light without any extra precautions taken against the presence of light. Still further embodiments relate to the drug product manufactured by the method of any of the methods of the current invention.

The process for manufacturing the drug product of the current invention will typically be performed as described in WO2015/128418 A1. Thus, the water used to prepare the solution is typically degassed or deaerated, distilled, sterile, pyrogen-free water for pharmaceutical use. According to some embodiments, the deoxygenated or degassed water is obtained by blowing or bubbling an inert gas current.

Phenylephrine and optionally any excipient(s) are dissolved in the degassed water. According to one preferred embodiment, dissolution can be carried out within a suitable inert container, in which air or oxygen have been removed by passage of inert gas. According to a further preferred embodiment, during dissolution of the phenylephrine an inert gas can be blown into the container or tank of the solution, to remove any residual oxygen. Thus, in all of the embodiments of the current invention, the formulations of the present invention generally comprise an inert gas such as nitrogen from the degassing procedure.

The drug product is sterilized by known means. Such known means in the art comprise e.g. sterile filtration, heat treatment and/or irradiation, in particular sterile filtration and/or heat treatment, with sterile filtration most preferred. The heat treatment, if performed, may be accomplished typically at temperatures above 100° C., for a time suitable for sterilization, for example equal to or greater than 15 minutes. Preferably, the heat treatment can be a heat sterilization for 15 minutes at 121° C., in particular in an autoclave.

The sterile filtration, if performed, may be done by passing the solution containing phenylephrine through a filter of the type for sterilization, as known in the art. Passage of the phenylephrine solution through the filter can be sped up by blowing a current of inert gas which acts as a carrier. Suitable filters are those used in the pharmaceutical technology for preparation of sterile injectable solutions.

The drug product is also hermetically sealed. Sealing can be done in any conventional way, taking care that during the sealing step oxygen (or air) is kept out of the container, e.g. by a flow of inert gas, applying a drop of liquid nitrogen into the container before sealing, or applying vacuum or an inert gas atmosphere.

Preferably, the steps of the process of producing a phenylephrine solution as disclosed herein are carried out in sterile environments in order to avoid bacterial contamination of the phenylephrine solution.

According to a further aspect of the present invention, the phenylephrine solution or drug product of the invention as described herein is used as a parenteral dosage form, in particular a ready-to-administer parenteral dosage form, preferably for use to maintain adequate blood pressure during anesthesia or to treat vascular failure in shock and shock-like states.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention.

Example 1. Exemplary Formulations

Semi-naked formulations of phenylephrine HCl at concentrations of 80 µg/mL and 400 µg/mL, in the absence of a stabilizing agent such as sodium metabisulfite, are exemplified in Tables 1a and 1b. Sodium chloride was added in an amount sufficient to render the solution substantially isotonic (270-300 mOsm); hydrochloric acid was added in an amount sufficient to produce a pH of from 3.0 to 5.0. Alkalizing agents such as sodium hydroxide were omitted. The formulations are suitable for packaging in a single use RTU pouch of 250 mL or other medically useful volume.

TABLE 1a

| (80 µg/mL formulation) | | |
| --- | --- | --- |
| Ingredient | Function | Concentration |
| Phenylephrine HCl* | Active ingredient | 0.08 g/L |
| Sodium chloride | Tonicity agent | 9.04 g/L |
| Water for injection | Diluent | 995.38 g/L |
| Hydrochloric acid | pH adjustment | q.s. to pH 3.0-5.0 |
| Nitrogen | Manufacturing agent | q.s. |

*Based on weight of hydrochloride salt.

TABLE 1b

| (400 µg/mL formulation) | | |
| --- | --- | --- |
| Ingredient | Function | Concentration |
| Phenylephrine HCl* | Active ingredient | 0.40 g/L |
| Sodium chloride | Tonicity agent | 9.04 g/L |
| Water for injection | Diluent | 995.06 g/L |
| Hydrochloric acid | pH adjustment | q.s. to pH 3.0-5.0 |
| Nitrogen | Manufacturing agent | q.s. |

*Based on weight of hydrochloride salt.

Example 2. Stability Results for 80 µg/mL and 400 µg/µL 250 mL Formulations

A study was undertaken to evaluate the stability of the semi-naked phenylephrine formulations described in Example 1 at different time points, when packaged in 250 mL polypropylene pouches. The particular pouch used for this example is marketed by Kuraray America, Inc. (Houston, Tex.) under the trade name EVAL™ L171B, and incorporates a three ply polypropylene/EVOH copolymer/polypropylene bag wall. Further details of the pouch are given in Example 4.

Pouches were filled in an inert nitrogen atmosphere to a solution volume of 250 ml with a slight overage, and a nominal headspace volume. The solution itself was purged with nitrogen prior to ingredients dissolution and filling into the pouches, such that oxygen content in the final solution was minimized. The pouches were subjected to accelerated stability conditions for up to six months (40° C., 75% RH). All testing was undertaken according to stability methods prescribed by the International Conference on Harmonization, ICH Q1A (R2) (effective 1 Aug. 2003). Results are reported in Tables 2a and 2b.

TABLE 2a

| (80 µg/mL Formulation) | | | | |
| --- | --- | --- | --- | --- |
| Test | T0 | 1 mo | 3 mo | 6 mo |
| pH | 3.0 | 3.0 | 3.0 | 3.1 |
| Phenylephrine | 100.6 | 100.4 | 100.7 | 100.6 |
| Impurity C (phenylephrone) | ND | ND | ND | ND |
| Single impurity | <0.05 | 0.05 | 0.06 | 0.08 |
| Total impurities | <0.05 | 0.05 | 0.06 | 0.14 |

TABLE 2b

| (400 µg/mL Formulation) | | | | |
| --- | --- | --- | --- | --- |
| Test | T0 | 1 mo | 3 mo | 6 mo |
| pH | 3.1 | 3.0 | 3.0 | 3.1 |
| Phenylephrine | 100.2 | 100.1 | 100.7 | 100.5 |
| Impurity C (phenylephrone) | ND | ND | ND | ND |
| Single impurity | 0.06 | 0.05 | 0.05 | 0.07 |
| Total impurities | 0.06 | 0.05 | 0.05 | 0.07 |

As can be seen, both formulations maintained excellent stability over time, with no amounts of Impurity C (phenylephrone) being observed, the oxidative by-product of phenylephrine.

Example 3. Effect of pH on Formulation Stability

In order to ensure the least possible degradation of the formulation, studies were conducted on a semi-naked formulation of phenylephrine HCl (0.1 mg/mL) containing only sodium chloride as a tonicity adjusting agent and hydrochloric acid as an acidifying agent. Hydrochloric acid was added during manufacture to arrive at four different batches having pH values ranging from 3.0 to 6.0. Two sterilization methods were used, overkill ("OK") terminal sterilization and FO sterilization. Each batch, identified by its own pH, was divided into two sub-batches and subjected to either OK or FO sterilization.

Phenylephrine HCl assay % for each of the batches and sub-batches was determined following a forced degradation study at 60° C. The results are reported in Table 3a and depicted in FIG. 1.

TABLE 3a

| (Phenylephrine HPLC Assay % (60° C.)) | | | | |
|---|---|---|---|---|
| In-process | Weeks | | | |
| Conditions | 0 | 2 | 6 | 8 |
| pH 3.0 - F0 | 100.5 | 101.3 | 100.9 | 100.5 |
| pH 3.0 - OK | 100.4 | 101.3 | 100.8 | 100.5 |
| pH 4.0 - F0 | 100.3 | 101.2 | 100.7 | 100.4 |
| pH 4.0 - OK | 100.2 | 101.1 | 100.7 | 100.4 |
| pH 5.0 - F0 | 100.1 | 100.7 | 99.1 | 98.7 |
| pH 5.0 - OK | 100.1 | 100.6 | 99.4 | 98.2 |
| pH 6.0 - F0 | 99.6 | 99.5 | 98.3 | 97.9 |
| pH 6.0 - OK | 99.5 | 100.1 | 98.6 | 97.5 |

Figure 2:
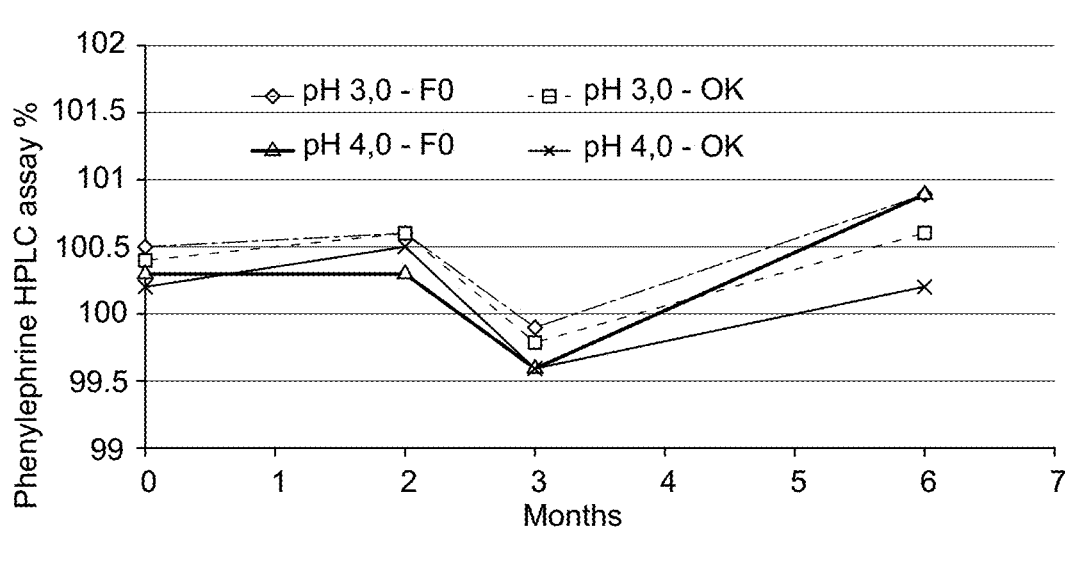
FIG. 2 is a graphical depiction of phenylephrine concen-trations measured by HPLC over time for the semi-naked formulations of the present invention, at pH values of 3.0 and 4.0, when stored at 40° C., as tested and described in Example 3.
Figure 3:
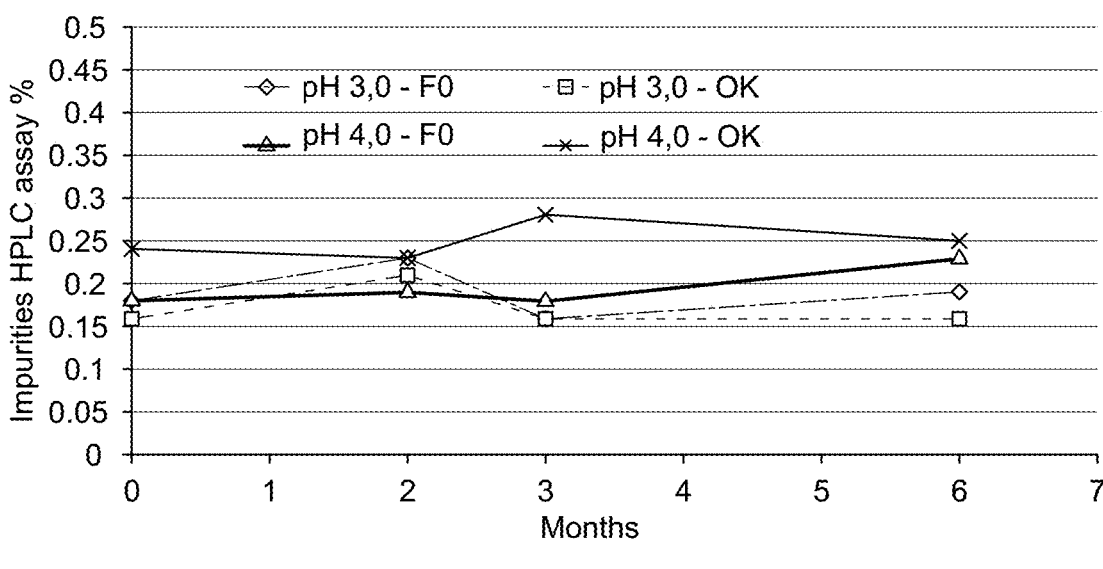
FIG. 3 is a graphical depiction of total impurities con-centrations measured by HPLC over time for the semi-naked formulations of the present invention, at pH values of 3.0 and 4.0, when stored at 40° C., as tested and described in Example 3.
Figure 4:
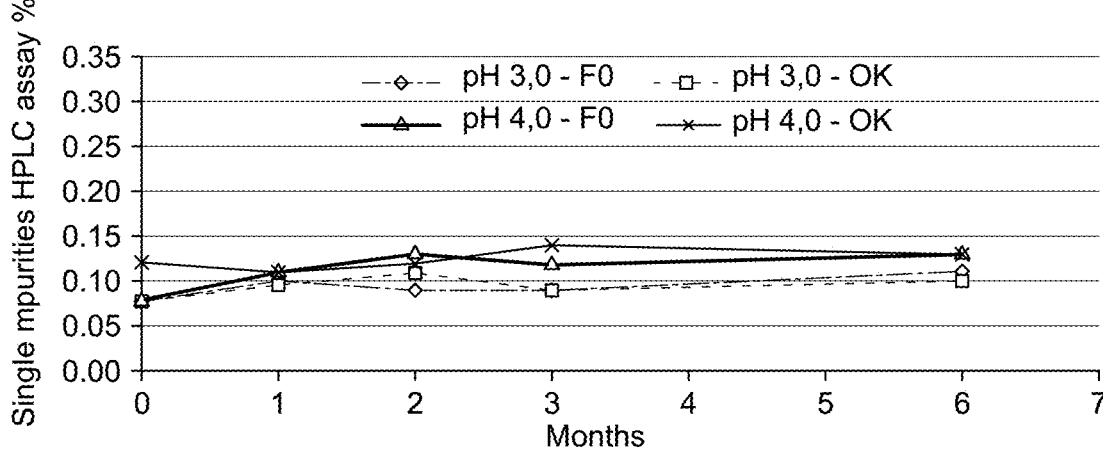
FIG. 4 is a graphical depiction of single impurity con-centrations measured by HPLC over time for the semi-naked formulations of the present invention, at pH values of 3.0 and 4.0, when stored at 40° C., as tested and described in Example 3.

Because the data indicated that the formulation was most stable at the lowest pH values, further studies were only undertaken using the 3.0 and 4.0 pH formulations, at 25° C. and 40° C. stability conditions. Data for phenylephrine assay %, and total and single unidentified impurities, during the 40° C. testing, are presented in Tables 3b, 3c, and 3d, and corresponding FIGS. 2, 3, and 4.

TABLE 3b

| (Phenylephrine HPLC Assay % (40° C.)) | | | | |
|---|---|---|---|---|
| In-process | Months | | | |
| Conditions | 0 | 1 | 2 | 3 | 6 |
| pH 3.0 - F0 | 100.5 | 101 | 100.6 | 99.9 | 100.9 |
| pH 3.0 - OK | 100.4 | 100.9 | 100.6 | 99.8 | 100.6 |
| pH 4.0 - F0 | 100.3 | 100.8 | 100.3 | 99.6 | 100.9 |
| pH 4.0 - OK | 100.2 | 100.8 | 100.5 | 99.6 | 100.2 |

TABLE 3c

| (Total Impurities HPLC Assay % (40° C.)) | | | | |
|---|---|---|---|---|
| In-process | Months | | | |
| Conditions | 0 | 1 | 2 | 3 | 6 |
| pH 3.0 - F0 | 0.18 | 0.18 | 0.23 | 0.16 | 0.19 |
| pH 3.0 - OK | 0.16 | 0.17 | 0.21 | 0.16 | 0.16 |
| pH 4.0 - F0 | 0.18 | 0.18 | 0.19 | 0.18 | 0.23 |
| pH 4.0 - OK | 0.24 | 0.17 | 0.23 | 0.28 | 0.25 |

TABLE 3d

| (Single Impurity HPLC Assay % (40° C.)) | | | | |
|---|---|---|---|---|
| In-process | Months | | | |
| Conditions | 0 | 1 | 2 | 3 | 6 |
| pH 3.0 - F0 | 0.08 | 0.10 | 0.09 | 0.09 | 0.11 |
| pH 3.0 - OK | 0.08 | 0.10 | 0.11 | 0.09 | 0.10 |
| pH 4.0 - F0 | 0.08 | 0.11 | 0.13 | 0.12 | 0.13 |
| pH 4.0 - OK | 0.12 | 0.11 | 0.12 | 0.14 | 0.13 |

In this series of experiments it can be seen that the pH 3.0 and pH 4.0 formulations performed similarly when subjected to FO sterilization. However, when subjected to overkill terminal sterilization, a clear preference was observed for the pH 3.0 formulation.

Example 4. Effect of Oxygen on Stability of Formulation

To determine the effect of oxygen on the stability of semi-naked 80 and 400 µg/mL formulations of phenylephrine when packaged in RTU drip pouches, the formulations were packaged into two different commercially available RTU pouches in nominal volumes of 250 mL. The selected pouches included a conventional polypropylene pouch, with no added protection against oxygen permeability, and a special polypropylene pouch manufactured specially to provide an enhanced oxygen barrier.

The conventional polypropylene pouch was manufactured using a single ply random copolymer polypropylene based on a phthalate-free catalyst, and is marketed by Total Research and Technology Feluy (Feluy, Belgium), under the trade name Polypropylene Aceso® PPM R020 S01. The enhanced oxygen barrier pouch employed a three ply polypropylene/EVOH copolymer/polypropylene bag wall with the EVOH copolymer being a 27 mol % Ethylene-Vinyl Alcohol Copolymer, and is marketed by Kuraray America, Inc. (Houston, Tex.) under the trade name EVAL™ L171B.

Figure 5:
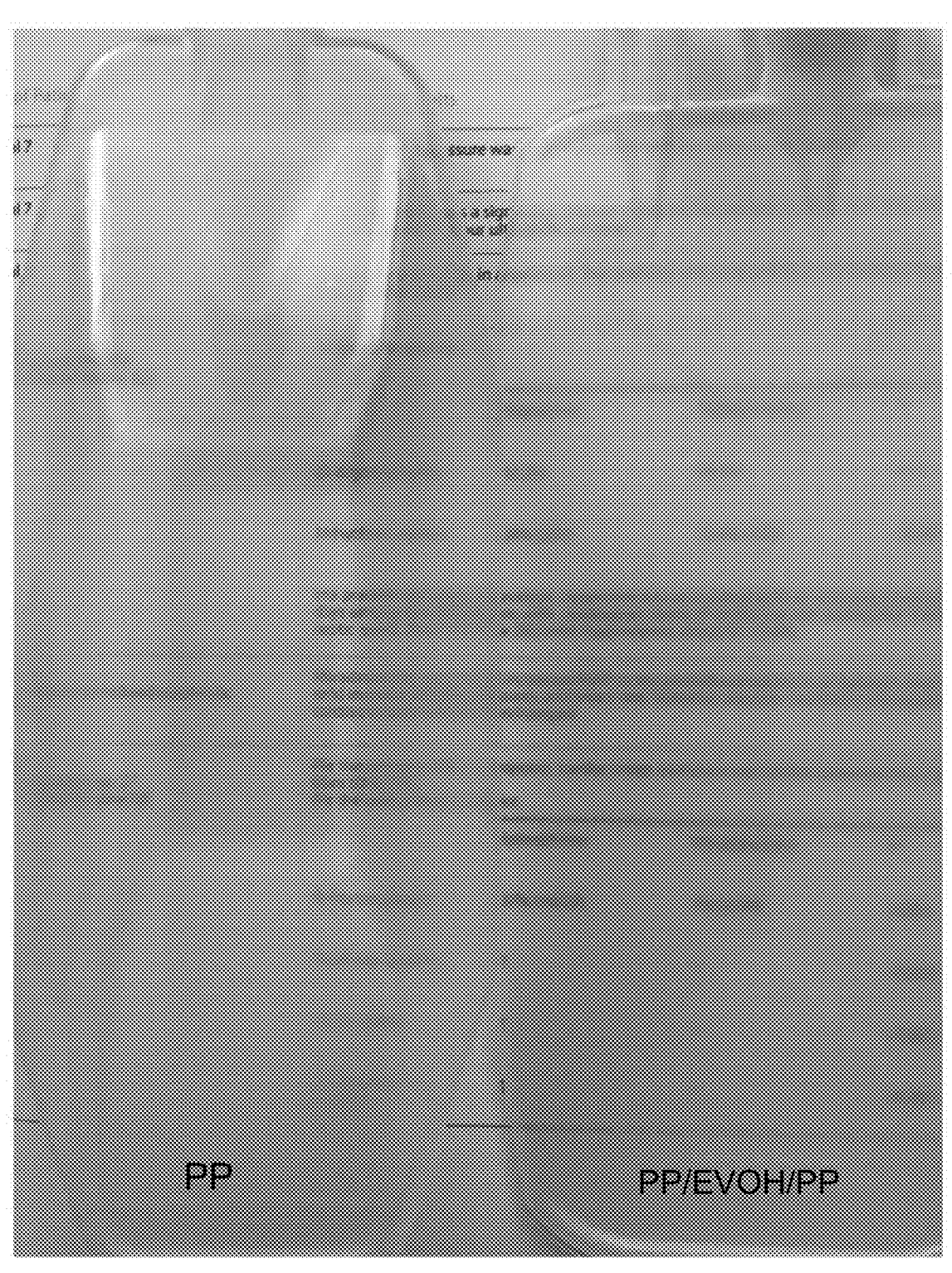
FIG. 5 is a photograph of the translucent polypropylene and polypropylene/ethylene vinyl alcohol/polypropylene bags described in Example 4, laid over a black and white image to illustrate contrast, haze, and luminous transmit-tance.

Polypropylene Aceso® PPM R020 S01 and EVAL™ L171B polymers are illustrated in FIG. 5, and characterized by physical properties reported in Tables 4a and 4b:

TABLE 4a

| (Polypropylene Aceso ® PPM R020 S01) | | | |
|---|---|---|---|
| | Method | Unit | Typical Value |
| Rheological Properties | | | |
| Melt Flow Index 230° C./2.16 kg | ISO 1133 | g/10 min | 1.8 |
| Mechanical Properties | | | |
| Tensile Strength at Yield | ISO 527-2 | MPa | 26 |
| Elongation at Yield | ISO 527-2 | % | 10 |
| Tensile Modulus | ISO 527-2 | MPa | 1000 |
| Flexural Modulus | ISO 178 | MPa | 900 |
| Izod Impact Strength (notched) at 23° C. | ISO 180 | kJ/m$^2$ | 6 |
| Charpy impact strength (notched) at 23° C. | ISO 179 | kJ/m$^2$ | 8 |
| Rockwell Hardness - R-scale | ISO 2039-2 | | 82 |
| Thermal Properties | | | |
| Melting Point | ISO 3146 | ° C. | 149 |
| Vicat Softening Point | ISO 306 | ° C. | |

TABLE 4a-continued

| (Polypropylene Aceso ® PPM R020 S01) | | | |
|---|---|---|---|
| | Method | Unit | Typical Value |
| 50N - 50° C. per hour | | | 67 |
| 10N - 50° C. per hour | | | 130 |
| | Method | Unit | Typical Value |
| Other Physical Properties | | | |
| Density | ISO 1183 | g/cm$^3$ | 0.902 |
| Bulk Density | ISO 1183 | g/cm$^3$ | 0.525 |

Table 4b (EVAL ™ L171B)

| | Unit | Test Method | Metric/(English) |
|---|---|---|---|
| Typical Properties | | | |
| MFR | g/10 min | ISO1133 (210° C.) | 4.0 |
| Density | 10$^3$ kg/m$^3$ | ISO1183-3 | 1.21 |
| Thermal Properties | | | |
| Melting Temp | ° C. (° F.) | ISO 11357 | 190 (374) |
| Crystallization Temp | ° C. (° F.) | ISO 11357 | 164 (327) |
| Glass Transition Point | ° C. (° F.) | ISO 11357 | 63 (145) |
| Vicat Softening Point | ° C. (° F.) | ISO 306 | 181 (358) |
| Mechanical Properties | | | |
| Tensile stress at break | MPa (psi) | ISO 527 | 41 (5,900) |
| Elongation at break | % | ISO 527 | 12 |
| Young's Modulus | GPa (psi) | ISO 527 | 4.9 (710,000) |
| Flexural Modulus | GPa (psi) | ISO 178 | 4.7 (680,000) |
| Charpy Impact Strength | kJ/m$^2$ (ft.lbf/in$^2$) | ISO 179-1 | 6 (3.0) |
| Rockwell Hardness | HRM | ISO 2039-2 | 97 |
| Barrier Properties (cast film) | | | |
| Oxygen Transmission Rate | cm$^3$ · 20 μm/m$^2$ · day · atm (cm$^3$ · mil/100 in$^2$ · day · atm) | ISO 14663-2 | 0.1 (0.005) |

The pouches were filled as described in Example 2, and tested for stability under room temperature and accelerated stability conditions. Results for accelerated stability testing (40° C., 75% RH) are presented below in Tables 4c, 4d, 4e, and 4f TABLE 4c

| (80 μg/mL) (Polypropylene Aceso ® PPM R020 S01) | | | | |
|---|---|---|---|---|
| Test | T 0 | 1 m | 3 m | 6 m |
| pH | 3.0 | 3.0 | 3.0 | 3.1 |
| Phenylephrine assay | 100.6 | 100.4 | 100.7 | 100.6 |
| Impurity C (phenylephrone) assay | ND | ND | ND | ND |
| Unknown impurities assay (main) | <0.05 | 0.05 | 0.06 | 0.08 |
| Total unknown impurities | <0.05 | 0.05 | 0.06 | 0.14 |

TABLE 4d

| (80 μg/mL) (EVAL ™ L171B) | | | | |
|---|---|---|---|---|
| Test | T 0 | 1 m | 3 m | 6 m |
| pH | 3.0 | 3.0 | 3.0 | 3.0 |
| Phenylephrine assay | 100.5 | 100.4 | 100.7 | 100.5 |
| Impurity C (phenylephrone) assay | ND | ND | ND | ND |

TABLE 4d-continued

| (80 μg/mL) (EVAL ™ L171B) | | | | |
|---|---|---|---|---|
| Test | T 0 | 1 m | 3 m | 6 m |
| Unknown impurities assay (main) | 0.10 | 0.08 | 0.07 | 0.10 |
| Total unknown impurities | 0.10 | 0.15 | 0.19 | 0.24 |

TABLE 4e

| (400 μg/mL) (Polypropylene Aceso ® PPM R020 S01) | | | | |
|---|---|---|---|---|
| Test | T 0 | 1 m | 3 m | 6 m |
| pH | 3.1 | 3.0 | 3.0 | 3.1 |
| Phenylephrine assay | 100.2 | 100.1 | 100.7 | 100.5 |
| Impurity C (phenylephrone) assay | ND | ND | ND | ND |
| Unknown impurities assay (main) | 0.06 | 0.05 | 0.05 | 0.07 |
| Total unknown impurities | 0.06 | 0.05 | 0.05 | 0.07 |

Table 4f (400 μg/mL) (EVAL ™ L171B)

| Test | T 0 | 1 m | 3 m | 6 m |
|---|---|---|---|---|
| pH | 3.1 | 3.0 | 3.0 | 3.1 |
| Phenylephrine assay | 100.2 | 100.1 | 100.6 | 100.4 |

-continued

| Table 4f (400 µg/mL) (EVAL ™ L171B) | | | | |
|---|---|---|---|---|
| Test | T 0 | 1 m | 3 m | 6 m |
| Impurity C (phenylephrone) assay | ND | ND | ND | ND |
| Unknown impurities assay (main) | 0.06 | 0.06 | 0.05 | 0.08 |
| Total unknown impurities | 0.06 | 0.06 | 0.05 | 0.08 |

As can be seen, both formulations performed equally well in both pouches, in spite of the conventional pouch's greater permeability to air and susceptibility to oxidative contamination. This result was very surprising considering phenylephrine's well-known propensity towards oxidative degradation, and the specific identification of Impurity C, a widely reported oxidative degradant of phenylephrine. A semi-naked formulation of phenylephrine that omits sodium bisulfite and sodium hydroxide, packaged in conventional RTU polypropylene pouches without any additional protection from oxygen, unexpectedly remains stable for extended periods of time even when subjected to forced degradation studies.

Example 5. Comparison to a Similar Drug Prone to Oxidative Degradation

In order to confirm the significance of the results from Example 4, and the surprising stability of the semi-naked phenylephrine formulations of the current invention, a comparison was made to a similar semi-naked formulation of noradrenaline bitartrate, a molecule also prone to oxidative degradation, in the Polypropylene Aceso® PPM R020 S01 and EVAL™ L171B pouches used in Example 4. The pouches were filled is a substantially similar manner to the pouches in Example 4. The noradrenaline bitartate formulation is reported in Table 5a:

TABLE 5a

| (32 µg/mL Noradrenaline Formulation) | | |
|---|---|---|
| Ingredient | Function | Concentration |
| Noradrenaline bitartrate* | Active ingredient | 0.032 g/L |
| Sodium chloride | Tonicity agent | 250-350 mOsm/kg |
| Water for injection | Diluent | q.s. |
| Hydrochloric acid | pH adjustment | q.s. to pH 3.0-4.5 |

*Based on weight of the free base.

The pouches were filled and tested for stability under room temperature and accelerated stability conditions. Results for accelerated stability testing (40° C., 75% RH) are presented below in Tables 4b and 4c.

TABLE 5b

| (32 µg/mL Noradrenaline) (Polypropylene Aceso ® PPM R020 S01) | | | | | |
|---|---|---|---|---|---|
| Test | T0 | 1 m | 2 m | 3 m | 6 m |
| pH | 3.1 | 3.1 | 3.1 | 3.1 | 3.3 |
| Noradrenaline assay | 100.7 | 98.3 | 96.5 | 93.4 | 87.8 |
| Arterenone assay | 0.01 | 0.09 | 0.13 | 0.20 | 0.28 |
| Total unknown impurities | 0.10 | 0.19 | 0.51 | 1.15 | 2.58 |

TABLE 5c

| (32 µg/mL Noradrenaline) (EVAL ™ L171B) | | | | | |
|---|---|---|---|---|---|
| Test | T0 | 1 m | 2 m | 3 m | 6 m |
| pH | 3.1 | 3.1 | 3.1 | 3.1 | 3.3 |
| Noradrenaline assay | 100.7 | 100.4 | 100.0 | 97.8 | 92.2 |
| Arterenone assay | 0.01 | 0.02 | 0.03 | 0.08 | 0.18 |
| Total unknown impurities | 0.09 | 0.11 | 0.19 | 0.30 | 1.52 |

In contrast to the results reported for phenylephrine in Example 4, semi-naked formulations of noradrenaline bitartrate were more stable when protected from oxygen and packaged in the EVAL™ L171B pouches. Less noradrenaline degraded, fewer impurities appeared, and less of the oxidative degradant (arterenone) was produced.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A drug product in a hermetically sealed intravenous ready to use collapsible drip bag, wherein:
   a) the bag comprises two opposed walls sealed around their peripheries comprising an inner ply of translucent or transparent polypropylene;
   b) the bag defines an interior volume;
   c) the interior volume comprises:
      i) a liquid volume comprising from 75 to 550 ml of a liquid formulation;
      ii) a gaseous headspace occupying from 0 to 25% of the interior volume;
   d) the liquid formulation comprises:
      i) phenylephrine or a pharmaceutically acceptable salt thereof at a concentration of from 0.001 to 2.0 mg/ml;
      ii) a tonicity agent;
      iii) an acidic pH adjusting agent; and
      iv) water;
   e) the liquid formulation has a pH of from 3.0 to 3.4; and
   f) the liquid formulation excludes antioxidants and chelating agents and contains no more than 1% degradants or impurities after three months storage at 40° C. and 75% relative humidity.

2. The drug product of claim 1, comprising phenylephrine hydrochloride at a concentration of 0.08 mg/ml or 0.4 mg/ml based on the weight of the hydrochloride salt.

3. The drug product of claim 1, in the absence of an antimicrobial preservative.

4. The drug product of claim 1, wherein the bag wall has an oxygen transmission rate greater than 100 cm$^3$·20 µm/m$^2$·day atm at room temperature and atmospheric pressure.

* * * * *